United States Patent
Dewey et al.

(10) Patent No.: US 11,534,339 B2
(45) Date of Patent: Dec. 27, 2022

(54) HIGH SPEED TRACKING OF IOL DURING REFRACTIVE INDEX MODIFICATION

(71) Applicant: AMO Development, LLC, Irvine, CA (US)

(72) Inventors: David A. Dewey, Sunnyvale, CA (US); Michael Wiltberger, Santa Clara, CA (US); Phillip Gooding, Mountain View, CA (US); Georg Schuele, Portola Valley, CA (US)

(73) Assignee: AMO Development, LLC, Irvine, CA (US)

( * ) Notice: Subject to any disclaimer, the term of this patent is extended or adjusted under 35 U.S.C. 154(b) by 0 days.

(21) Appl. No.: 17/057,686

(22) PCT Filed: Apr. 9, 2020

(86) PCT No.: PCT/IB2020/053420
§ 371 (c)(1),
(2) Date: Nov. 22, 2020

(87) PCT Pub. No.: WO2020/208584
PCT Pub. Date: Oct. 15, 2020

(65) Prior Publication Data
US 2022/0047424 A1    Feb. 17, 2022

Related U.S. Application Data

(60) Provisional application No. 62/944,335, filed on Dec. 5, 2019, provisional application No. 62/832,836, filed on Apr. 11, 2019.

(51) Int. Cl.
*A61F 9/008* (2006.01)
*G16H 30/40* (2018.01)

(52) U.S. Cl.
CPC ......... *A61F 9/00834* (2013.01); *G16H 30/40* (2018.01); *A61F 2009/0087* (2013.01);
(Continued)

(58) Field of Classification Search
CPC ........ A61F 9/00834; A61F 2009/00842; A61F 2009/00846; A61F 2009/0087
See application file for complete search history.

(56) References Cited

U.S. PATENT DOCUMENTS 5,943,117 A * 8/1999 Van de Velde ...... A61B 3/1025
351/205
8,845,625 B2 9/2014 Angeley et al.
(Continued)

FOREIGN PATENT DOCUMENTS

KR    20120111792 A    10/2012

OTHER PUBLICATIONS

Vass C, Rigby D, Tate K, Stewart A, Payne K. An Exploratory Application of Eye-Tracking Methods in a Discrete Choice Experiment. Med Decis Making. Aug. 2018;38(6):658-672. doi: 10.1177/0272989X18782197. PMID: 30074879; PMCID: PMC6088456. (Year: 2018).*
(Continued)

*Primary Examiner* — Nathan J Jenness
(74) *Attorney, Agent, or Firm* — Johnson & Johnson Surgical Vision, Inc.

(57) ABSTRACT

During a process of refractive index modification of an intraocular lens (IOL) using an ophthalmic laser system, optical position monitoring of the IOL is performed by a video camera system viewing the top surface of the IOL. Fiducials are incorporated into the IOL at manufacture, or created in-vivo with laser. The monitoring method employs a defined area of interest (AOI) to limit the number of pixels to be analyzed, to achieve adequately high acquisition speed.

(Continued)

In one example, the AOI contains 5 camera scan line segments, each line segment having sufficient pixels to create a stable amplitude signature. Successive frames of the AOI are analyzed to detect movement of the fiducial and/or to determine whether the fiducial has been lost.

22 Claims, 3 Drawing Sheets

(52) U.S. Cl.
     CPC ............... *A61F 2009/00842* (2013.01); *A61F 2009/00846* (2013.01)

(56) References Cited

U.S. PATENT DOCUMENTS

| | | | |
|---|---|---|---|
| 2009/0093798 A1* | 4/2009 | Charles | A61F 9/0079 606/4 |
| 2012/0310223 A1* | 12/2012 | Knox | A61F 9/00827 606/5 |
| 2018/0008462 A1 | 1/2018 | Zickler et al. | |
| 2018/0242840 A1 | 8/2018 | Copland | |
| 2019/0201188 A1* | 7/2019 | Kondis | G02B 27/0093 |
| 2019/0307554 A1 | 10/2019 | Schuele et al. | |

OTHER PUBLICATIONS

Porter, Jason PhD*; Yoon, Geunyoung PhD; MacRae, Scott MD; Pan, Gang PhD; Twietmeyer, Ted; Cox, Ian G. PhD; Williams, David R. PhD Surgeon offsets and dynamic eye movements in laser refractive surgery. Journal of Cataract & Refractive Surgery: Nov. 2005—vol. 31—Issue 11—p. 2058-2066 (Year: 2005).*

International Search Report and Written Opinion for Application No. PCT/IB2020/053420, dated Jun. 25, 2020, 6 pages.

Ma, H., et al., "A Simple Marker-Assisted 3D NanometerDrift Correction Method for Superresolution Microscopy," Biophysical Journal, May 2017, vol. 112 (10),pp. 2196-2208, ISSN 0006-3495, (https://doi:10.1016/j.bpj.2017.04.025).paragraphs "Introduction","Optical imaging system","Marker-assisted 3D online Drift Correction Method","Method to estimate 3D position from the fiducial markers", "Reconstruction of SuperresolutionImage".

Raith e_LiNE Software Operation Manual, Apr. 10, 2005, "Mix & Match Exposure".

* cited by examiner

HIGH SPEED TRACKING OF IOL DURING REFRACTIVE INDEX MODIFICATION

CROSS-REFERENCES TO RELATED APPLICATIONS

This application is a U.S. national stage of and claims the benefit under 35 U. S. C. § 371 of International Patent Application No. PCT/IB2020/053420, filed Apr. 9, 2020, which claims priority to and incorporates by reference the entire contents of U.S. Provisional Application No. 62/832,836, filed Apr. 11, 2019 and U.S. Provisional Application No. 62/944,335, filed Dec. 5, 2019, all of which are incorporated herein by reference in their entirety.

BACKGROUND OF THE INVENTION

Field of the Invention

This invention relates to a process of modifying refractive properties of an intraocular lens (IOL) using an ophthalmic laser system, and in particular, it relates to a method for tracking movements of the IOL during the modification.

Description of Related Art

Laser refractive index modification (or "writing") of in-vivo IOLs may require lateral spatial control of the written pattern to the micron level. This may be needed to assure fidelity of the intended optical modification. In some applications, optical modifications of the IOL created by laser refractive index writing require creation of planar patterns of concentric circles with radial spacing at the micron level. It may also require interlacing of individual laser exposures within a given circle spatially controlled to the micron level.

Many current techniques employed for laser treatment of the eye rely on mechanical stabilization by direct contact of the ophthalmic laser device with the eye's exterior. This may not sufficiently control movement of the IOL suspended by tissue within the eye's interior.

SUMMARY

The present invention is directed to an optical position monitoring method and related apparatus which can be used to tract the position of the IOL during refractive index modification.

An object of the present invention is to provide high speed tracking of the IOL during refractive index modification.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a process of modifying an intraocular lens (IOL) implanted in a patient's eye using an ophthalmic laser system, which includes: delivering a laser beam into the IOL to modify a refractive property of the IOL; simultaneously monitoring a position of the IOL within the eye, which includes: operating a video camera to acquire an image of a field of view containing the IOL; performing a contrast analysis on the image to locate a high contrast fiducial of the IOL; obtaining a reference area of interest (AOI) from the image, the reference AOI being centered around the fiducial and containing a predefined number of video camera scan line segments with a predefined number of pixels per scan line segment; operating the video camera to obtain multiple successive AOIs from successive images, each AOI containing the predefined number of video camera scan line segments with the predefined number of pixels per scan line segment; and analyzing each of the multiple successive AOIs to determine a direction and magnitude of movement of the fiducial; and controlling delivery of the laser beam into the IOL based on the direction and/or magnitude of movement of the fiducial.

In another aspect, the invention provides an ophthalmic surgical laser system for modifying an intraocular lens (IOL) implanted in a patient's eye, the system including: a laser light source configured to generate a laser beam; an optical delivery system configured to deliver the laser beam to the IOL, including a scanner system configured to scan the laser beam within the IOL; a video camera configured to acquire an image of a field of view containing the IOL; and a controller configured to control the laser light source and the scanner system to deliver the laser beam in the IOL to modify a refractive property of the IOL, the controller being programmed to simultaneously monitor a position of the IOL within the eye, including: to operate a video camera to acquire an image of a field of view containing the IOL; to perform a contrast analysis on the image to locate a high contrast fiducial of the IOL; to obtain a reference area of interest (AOI) from the image, the reference AOI being centered around the fiducial and containing a predefined number of video camera scan line segments with a predefined number of pixels per scan line segment; to operate the video camera to obtain multiple successive AOIs from successive images, each AOI containing the predefined number of video camera scan line segments with the predefined number of pixels per scan line segment; and to analyze each of the multiple successive AOIs to determine a direction and magnitude of movement of the fiducial; and wherein the controller is further configured to control delivery of the laser beam into the IOL based on the direction and/or magnitude of movement of the fiducial.

It is to be understood that both the foregoing general description and the following detailed description are exemplary and explanatory and are intended to provide further explanation of the invention as claimed.

DETAILED DESCRIPTION OF PREFERRED EMBODIMENTS

Commonly owned, co-pending U.S. patent application Ser. No. 16/375,784, filed Apr. 4, 2019, entitled Methods and Systems for Changing a Refractive Property of an Implantable Intraocular Lens ("the '784 application"), describes a "method of altering a refractive property of a crosslinked acrylic polymer material by irradiating the material with a high energy pulsed laser beam to change its refractive index. The method is used to alter the refractive property, and hence the optical power, of an implantable intraocular lens after implantation in the patient's eye. In some examples, the wavelength of the laser beam is in the far red and near IR range and the light is absorbed by the crosslinked acrylic polymer via two-photon absorption at high laser pulse energy. . . . The method can be used to form a Fresnel lens in the optical zone [of the IOL]." (Abstract.) As described in the '784 application, the IOL may be formed of a crosslinked acrylic polymer, and the refractive index modification is achieved through heating of the material. The laser beam may be in the blue range, or the red and near infrared range, in which case the IOL material absorbs the laser light through two-photon absorption. The content of the '784 application is incorporated herein by reference in its entirety.

Embodiments of the present invention provide a method to track movement of the IOL optically at sufficient resolution and speed to enable either real time modification of the pattern writing to account for the IOL movement, or cessation of writing and continuation after movement has stopped.

Figure 1:
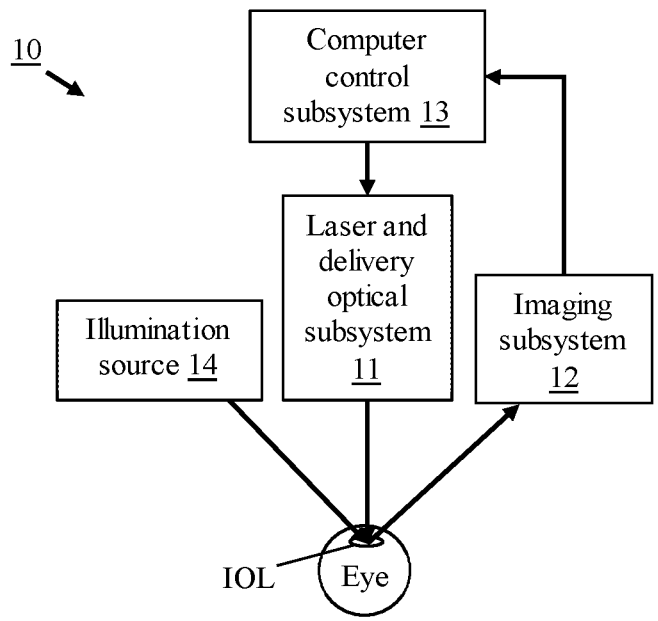
FIG. 1 schematically illustrates an ophthalmic laser surgical system in which embodiments of the present invention may be implemented.
Figure 2:
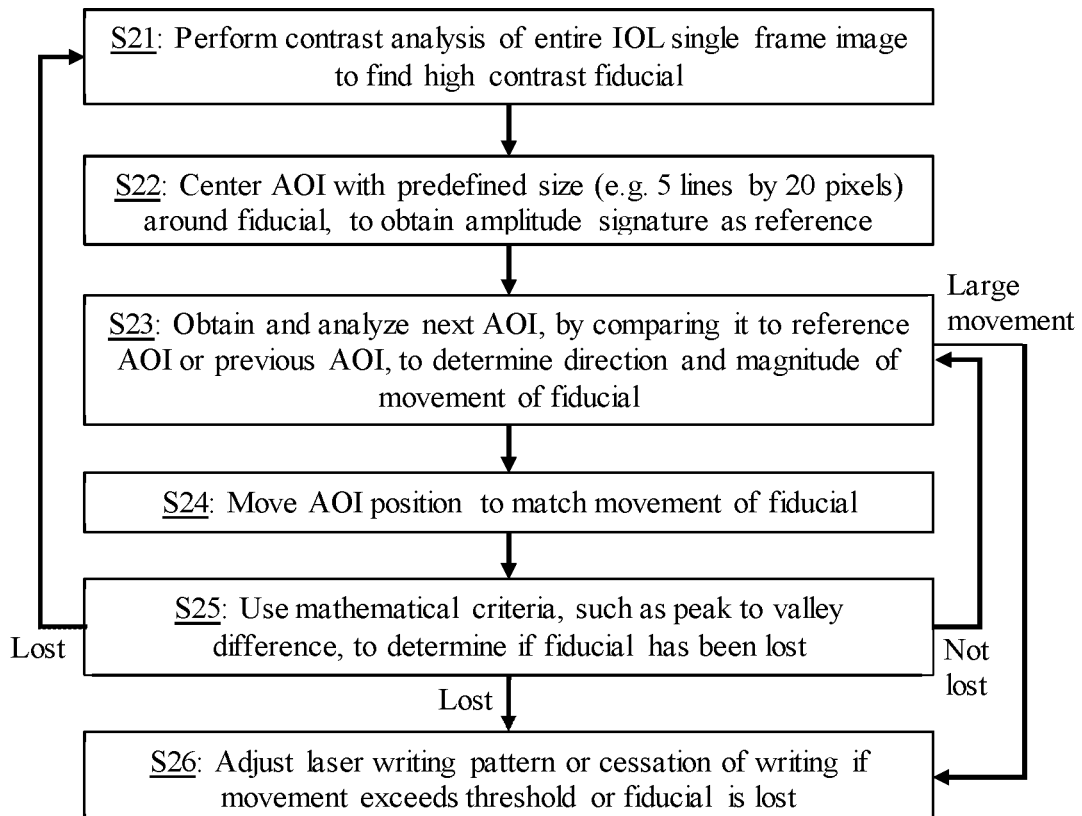
FIG. 2 schematically illustrates an optical tracking method performed during laser modification of an IOL according to embodiments of the present invention.

FIG. 1 schematically illustrates an ophthalmic laser surgical system 10 in which embodiments of the present invention may be implemented. The system 10 includes a laser device and associated beam delivery optical subsystem 11 for delivering a pulsed laser beam to the eye for treatment, an imaging subsystem 12 for detecting a signal from the eye, and a computer control subsystem 13 that performs control and data processing functions. In some embodiments, the system also includes an external illumination source 14. The imaging subsystem 12 may be implemented by different devices in the different embodiments described below. Although not shown in FIG. 1, the imaging subsystem 12 and the beam delivery optical subsystem 11 may share certain optical components in some embodiments. Many types of ophthalmic laser surgical system are known in the art and their detailed descriptions are omitted here. For example, commonly owned U.S. Pat. No. 8,845,625, which is incorporated herein by reference in its entirely, discloses in its FIGS. 1-4 and accompanying descriptions in the specification, an ophthalmic laser surgical system that includes an ultrafast laser source, a beam delivery optical subsystem including scanning devices, an OCT subsystem, an imaging subsystem such as a video monitoring subsystem for viewing an image of the eye, an aim beam subsystem, and related control subsystem.

In embodiments of the present invention, optical position monitoring may be performed by one or more video cameras of the imaging subsystem 12 viewing the top surface of the IOL. The cameras may operate dynamically to first locate IOL edges or other fiducials, then zoom to that area to increase resolution. The position monitoring is performed simultaneously with the delivery of laser beam to the IOL to treat the IOL.

The cameras may track orthogonal IOL edges for tracking translation movement only, or track two visible fiducials on the IOL to monitor both translation and rotational movement. Fiducials may be incorporated into the IOL at manufacture, or created in-vivo with laser. The fiducial writing may be performed by the index writing laser, or by another laser dedicated to that task.

Figure 5:
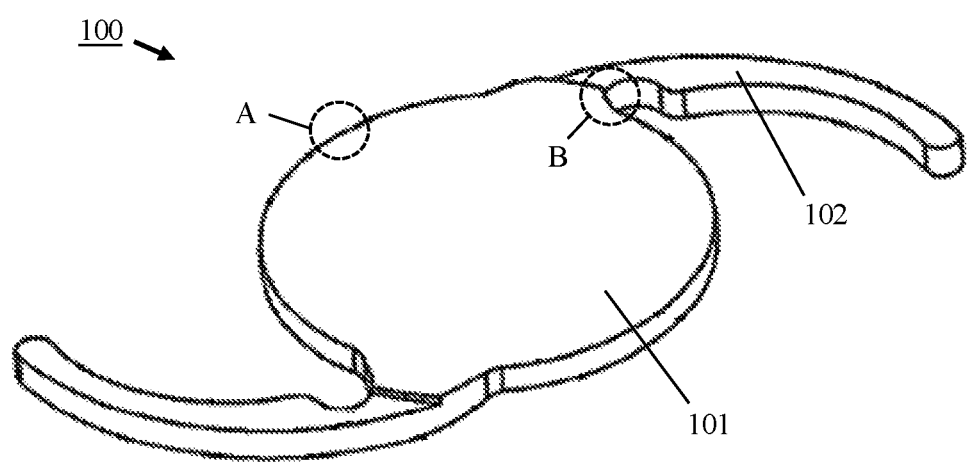
FIG. 5 schematically illustrates an IOL bearing fiducials.

For example, as schematically illustrated in FIG. 5, the area A contains an edge of the optic 101 of the IOL 100, which may be monitored to detect a translation movement of the IOL in the direction perpendicular to that edge. In another example, a part of the IOL that has a distinctive shape, such as a corner where the haptic 102 of the IOL joins the optic 101 as indicated by area B in FIG. 5, may be monitored to detect translation as well as rotation of the IOL. A visible defect in the IOL may also be monitored to detect translation and/or rotation of the IOL. More generally, any visually recognizable feature of the IOL that can be used to monitor movement of the IOL may be referred to as a fiducial, be it intrinsic features of the IOL or features specifically formed in the IOL for monitoring purpose.

With current digital camera technology, limiting the number of pixels to be analyzed by employing defined areas of interest (AOI) is preferred to achieve adequately high acquisition speed. In one embodiment, the following process is employed to dynamically select the minimal AOI (refer to FIG. 2).

Figure 3:
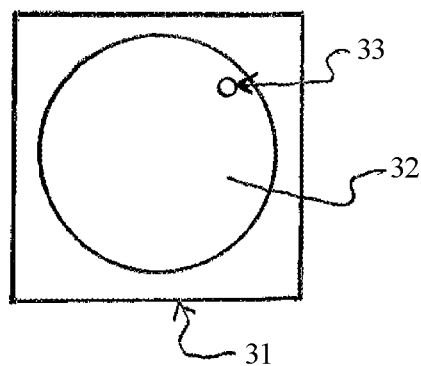
FIG. 3 depicts an exemplary field of view of the camera during optical tracking.

First, contrast analysis is performed of the entire IOL single frame image to find high contrast fiducials (step S21). Any suitable methods for calculating local contrast of an image may be used in this step. The purpose is to find areas with high local contrast to be used as fiducials. FIG. 3 depicts an IOL surface 32 seen within the camera field of view 31, with a fiducial 33 on the IOL surface. Such a fiducial will generate comparatively high local contrast and will by identified as a fiducial in step S21. If multiple fiducials are identified, one of them is selected for monitoring.

Figure 4:
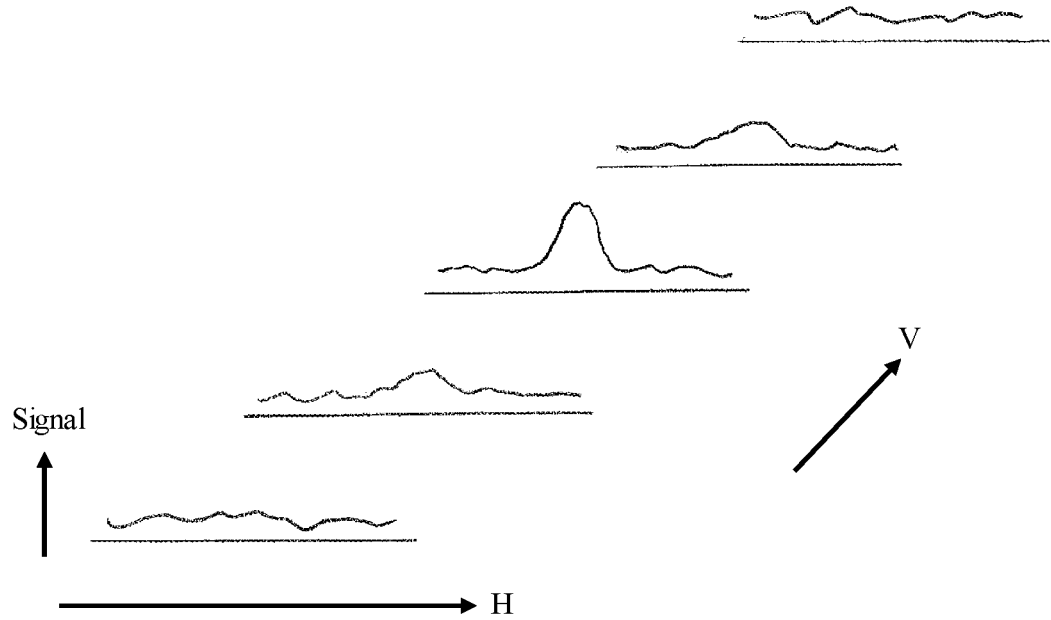
FIG. 4 illustrates an exemplary area of interest around a fiducial used for optical tracking according to an embodiment of the present invention.

Next, an AOI of the image is generated, which has a predefined size and is centered around the identified fiducial (step S22). As a video frame captured by the video camera is formed of multiple horizontal scan lines extending in the horizontal direction, the AOI is preferably a rectangular area containing a defined number of scan line segments. The vertical size of the AOI is the number of scan lines segments, and the horizontal size of the AOI is the number of pixels in each scan line segment. In a preferred embodiment, the size of the AOI is 5 lines in the vertical direction and 20 pixels in the horizontal direction. This size can create a stable amplitude signature, which is used as the reference signature. Here, the amplitude is, e.g., the brightness of the video signal. FIG. 4 depicts an exemplary AOI containing 5 scan line segments. In this illustrated example, the third (center) line contains a relatively high peak corresponding to the location of the fiducial, and the second and fourth lines each contain a lower peak. This corresponds to a dot shaped fiducial such as that shown in FIG. 3. Note that other sizes for the AOI can be used, such as 5 to 15 lines by 20 to 60 pixels, and the invention is not limited to any specific size of the AOI. Also note that the AOI is considered to be centered around the fiducial if the peak of the fiducial is within a predefined number (e.g., 1, or 2) of pixels and lines from the geometric center of the AOI.

Then, as the camera continues to acquire video images, successive AOIs are respectively obtained from successive video frames and analyzed, by comparing the amplitude signals of the AOI to the reference signature, or by comparing the amplitude signals of successive AOIs to each other, to determine a direction and magnitude of movement of the fiducial and to track the fiducial (steps S23-S25).

More specifically, after the next AOI is obtained, the AOI is analyzed, for example by using a statistical model, such as least squares fit, to determine the direction and magnitude of movement of the fiducial (step S23). In one embodiment, each line of the new AOI is fitted to each line of the reference AOI (the AOI generated in step S22) or the previous AOI to find the best-fitting pair of lines in the two AOIs, which gives the movement of the fiducial in the vertical direction. A pixel shift in the horizontal direction may be calculated when fitting each pair of lines, which gives the movement of the fiducial in the horizontal direction. In another embodiment, each AOI is expressed as a 2-dimensional matrix, the matrices of the current AOI and the reference or previous AOI are compares to calculate the vertical and horizontal movements of the fiducial. Any suitable techniques may be used to perform such line fitting of matrix comparison, many of which are available from open-source libraries. When a movement of the fiducial is detected in step S23, the AOI position may be moved (re-centered) to match the movement of the fiducial (step S24) before obtaining the next AOI.

Optionally, the current AOI may be analyzed using mathematical criteria, such as peak to valley difference, to determine whether the reference signature of the fiducial has been lost (step S25). For example, if the peak to valley difference value of the current AOI is smaller than that of the reference AOI or the previous AOI by more than a predetermined threshold, then the signature is deemed lost (i.e., the fiducial is no longer present in the AOI). If the signature is lost, the process may be restarted from step S21 to re-identify a fiducial, or the laser writing process may be paused (step S26). Step S25 is optional, and may be performed for each new AOI or performed from time to time for selected AOIs.

In steps S22 and S23, to obtain the AOI, a first method is to read out the entire video frame, i.e., data from the entire detector array of the camera (e.g., a CCD, CMOS, etc. detector array), and then take the desired portion from the read-out data (the entire frame) as the AOI. A second method is to only read out the desired portion of the detector array that corresponds to the AOI, and to use the read-out data directly as the AOI. Some commercially available cameras has the capability of being programed to read out only desired portions. The second method has the advantage of a faster readout speed. A third method combines the first and second method, by first reading out a portion the detector array corresponding to an area containing but is larger than the AOI (but not the entire array), and then taking a desired portion of the read-out data as the AOI. The size of the read-out area may be, for example, 7 lines or 9 lines, or 3×3 or 2×2 of the AOI size, etc. Using such a combined method, when the fiducial moves, the AOI may be moved (in step S24) by moving the AOI within the same read-out area, without having to re-program the camera to change the read-out area for each AOI movement, so long as the new AOI is still within the larger read-out area. In some embodiments, a further sampling may be performed on the AOIs to reduce their size prior to analysis.

The data analysis steps in the above process may be performed by the computer control subsystem 13.

As seen above, an important feature of preferred embodiments of the present invention is the use of an AOI which is a sub-portion of, and much smaller than, the entire video frame. Another important feature is the use of a fast algorithm to compare successive AOIs, such as by using a line-by-line comparison. Both of these features speed up data processing and allow for monitoring of the fiducial movement in real time while the treatment laser beam is being delivered to the IOL.

The above-described tracking process may be implemented using digital video cameras. The digital cameras is configured to use the above-described AOI process and can operate at high detection frame rate of over 1 kHz. The camera and the associated control system can be switched from full frame read-out to reading out the defined AOI area with low latency, preferably much less than 1 millisecond.

As mentioned earlier, tracking the AOI enables real time modification of the laser writing pattern to account for the IOL movement, or pausing of writing and continuation after movement has stopped. Such adjustment or pausing (step S26) may be performed, by the computer control subsystem 13, either in response to a fiducial movement greater or faster than a predetermined movement threshold (after step S23), or in response to the fiducial having been lost (after step S25).

In addition to position tracking of an IOL, the above-described method may be generally applied to any camera tracking application where the view has sufficiently high contrast and contains stable fiducials.

It will be apparent to those skilled in the art that various modification and variations can be made in the high speed IOL tracking method and related apparatus of the present invention without departing from the spirit or scope of the invention. Thus, it is intended that the present invention cover modifications and variations that come within the scope of the appended claims and their equivalents.

What is claimed is:

1. A process of modifying an intraocular lens (IOL) implanted in a patient's eye using an ophthalmic laser system, comprising:
   delivering a laser beam into the IOL to modify a refractive property of the IOL;
   simultaneously monitoring a position of the IOL within the eye, which includes:
      operating a video camera to acquire an image of a field of view containing the IOL;
      performing a contrast analysis on the image to locate a high contrast fiducial of the IOL;
      obtaining a reference area of interest (AOI) from the image, the reference AOI being centered around the fiducial and containing a predefined number of video camera scan line segments with a predefined number of pixels per scan line segment, wherein the predefined number of video camera scan line segments is from 5 to 15 and the predefined number of pixels per scan line segment is from 20 to 60;
      operating the video camera to obtain multiple successive AOIs from successive images, each AOI containing the predefined number of video camera scan line segments with the predefined number of pixels per scan line segment; and
      analyzing each of the multiple successive AOIs, without analyzing any image portions of the successive images other than the AOI, to determine a direction and magnitude of movement of the fiducial; and
   controlling delivery of the laser beam into the IOL based on the direction and/or magnitude of movement of the fiducial.

2. The method of claim 1, wherein the predefined number of video camera scan line segments in each AOI is 5 and the predefined number of pixels per scan line segment is 20.

3. The method of claim 1, wherein the step of analyzing each AOI includes comparing, by using a least squares fit, each scan line segment of the AOI with each scan line segment of the reference AOI or of a previous one of the AOIs, to obtain a best-fitting pair of scan line segments in the two AOIs which indicates the direction and magnitude of movement.

4. The method of claim 1, wherein the simultaneously monitoring step further includes:

after determining the direction and magnitude of movement of the fiducial by analyzing each AOI, adjusting a position of a next AOI based on the determined direction and magnitude of movement before obtaining the next AOI.

5. The method of claim 1, wherein the controlling step includes: when the magnitude of movement of the fiducial determined in the analyzing step is greater than a predetermined movement threshold, pausing delivery of the laser beam into the IOL.

6. The method of claim 1, wherein the simultaneously monitoring step further includes, for each of at least some of the multiple AOIs:
comparing a peak to valley difference value of the AOI with a peak to valley difference value of the reference AOI or of a previous one of the AOIs; and
when the peak to valley difference value of the AOI is smaller than the peak to valley difference value of the reference AOI or the previous AOI by more than a predetermined threshold, re-performing the steps of operating the video camera to acquire an image of a field of view containing the IOL, performing a contrast analysis on the image to locate a high contrast fiducial of the IOL, and obtaining a reference AOI from the image centered around the fiducial.

7. The method of claim 1, wherein the simultaneously monitoring step further includes, for each of at least some of the multiple AOIs:
comparing a peak to valley difference value of the AOI with a peak to valley difference value of the reference AOI or of a previous one of the AOIs; and
wherein the controlling step further includes: when the peak to valley difference value of the AOI is smaller than the peak to valley difference value of the reference AOI or the previous AOI by more than a predetermined threshold, pausing delivery of the laser beam into the IOL.

8. The method of claim 1, wherein the step of operating the video camera to obtain multiple successive AOIs includes, for each AOI:
operating the camera to read out data from an entire detector array of the camera; and
defining an area of the read-out data at a defined location containing the predefined number of scan line segments with the predefined number of pixels per scan line segment as the AOI.

9. The method of claim 1, wherein the step of operating the video camera to obtain multiple successive AOIs includes, for each AOI:
operating the camera to read out only a portion of a detector array of the camera as the AOI, the portion being located at a defined location and having the predefined number of scan line segments with the predefined number of pixels per scan line segment.

10. The method of claim 1, wherein the step of operating the video camera to obtain multiple successive AOIs includes, for each AOI:
operating the camera to read out only a portion of a detector array of the camera, the portion being located at a first defined location and having more scan line segments than the predefined number of scan line segments with more pixels per scan line segment than the predefined number of pixels per scan line segment; and
defining an area of the read-out data at a second defined location containing the predefined number of scan line segments with the predefined number of pixels per scan line segment as the AOI.

11. The method of claim 1, wherein the step of operating the video camera to obtain multiple successive AOIs and the step of analyzing each of the multiple successive AOIs are performed at a rate of over 1 kHz.

12. An ophthalmic surgical laser system for modifying an intraocular lens (IOL) implanted in a patient's eye, the system comprising:
a laser light source configured to generate a laser beam;
an optical delivery system configured to deliver the laser beam to the IOL, including a scanner system configured to scan the laser beam within the IOL;
a video camera configured to acquire an image of a field of view containing the IOL; and
a controller configured to control the laser light source and the scanner system to deliver the laser beam in the IOL to modify a refractive property of the IOL, the controller being programmed to simultaneously monitor a position of the IOL within the eye, including:
to operate the video camera to acquire an image of a field of view containing the IOL;
to perform a contrast analysis on the image to locate a high contrast fiducial of the IOL;
to obtain a reference area of interest (AOI) from the image, the reference AOI being centered around the fiducial and containing a predefined number of video camera scan line segments with a predefined number of pixels per scan line segment, wherein the predefined number of video camera scan line segments is from 5 to 15 and the predefined number of pixels per scan line segment is from 20 to 60;
to operate the video camera to obtain multiple successive AOIs from successive images, each AOI containing the predefined number of video camera scan line segments with the predefined number of pixels per scan line segment; and
to analyze each of the multiple successive AOIs, without analyzing any image portions of the successive images other than the AOI, to determine a direction and magnitude of movement of the fiducial; and
wherein the controller is further configured to control delivery of the laser beam into the IOL based on the direction and/or magnitude of movement of the fiducial.

13. The ophthalmic surgical laser system of claim 12, wherein the predefined number of video camera scan line segments in each AOI is 5 and the predefined number of pixels per scan line segment is 20.

14. The ophthalmic surgical laser system of claim 12, wherein the step of analyzing each AOI includes comparing, by using a least squares fit, each scan line segment of the AOI with each scan line segment of the reference AOI or of a previous one of the AOIs, to obtain a best-fitting pair of scan line segments in the two AOIs which indicates the direction and magnitude of movement.

15. The ophthalmic surgical laser system of claim 12, wherein the controller is further programed to:
after determining the direction and magnitude of movement of the fiducial by analyzing each AOI, adjust a position of a next AOI based on the determined direction and magnitude of movement before obtaining the next AOI.

16. The ophthalmic surgical laser system of claim 12, wherein the controller is further programed to:

when the magnitude of movement of the fiducial determined in the analyzing step is greater than a predetermined movement threshold, pause delivery of the laser beam into the IOL.

17. The ophthalmic surgical laser system of claim 12, wherein the controller is further programed to, for each of at least some of the multiple AOIs:
compare a peak to valley difference value of the AOI with a peak to valley difference value of the reference AOI or of a previous one of the AOIs; and
when the peak to valley difference value of the AOI is smaller than the peak to valley difference value of the reference AOI or the previous AOI by more than a predetermined threshold, re-perform the steps of operating the video camera to acquire an image of a field of view containing the IOL, performing a contrast analysis on the image to locate a high contrast fiducial of the IOL, and obtaining a reference AOI from the image centered around the fiducial.

18. The ophthalmic surgical laser system of claim 12, wherein the controller is further programed to, for each of at least some of the multiple AOIs:
compare a peak to valley difference value of the AOI with a peak to valley difference value of the reference AOI or of a previous one of the AOIs; and
when the peak to valley difference value of the AOI is smaller than the peak to valley difference value of the reference AOI or the previous AOI by more than a predetermined threshold, pause delivery of the laser beam into the IOL.

19. The ophthalmic surgical laser system of claim 12, wherein the controller is programed to, when obtaining each AOI:
operate the camera to read out data from an entire detector array of the camera; and
define an area of the read-out data at a defined location containing the predefined number of scan line segments with the predefined number of pixels per scan line segment as the AOI.

20. The ophthalmic surgical laser system of claim 12, wherein the controller is programed to, when obtaining each AOI:
operate the camera to read out only a portion of a detector array of the camera as the AOI, the portion being located at a defined location and having the predefined number of scan line segments with the predefined number of pixels per scan line segment.

21. The ophthalmic surgical laser system of claim 12, wherein the controller is programed to, when obtaining each AOI:
operate the camera to read out only a portion of a detector array of the camera, the portion being located at a first defined location and having more scan line segments than the predefined number of scan line segments with more pixels per scan line segment than the predefined number of pixels per scan line segment; and
define an area of the read-out data at a second defined location containing the predefined number of scan line segments with the predefined number of pixels per scan line segment as the AOI.

22. The ophthalmic surgical laser system of claim 12, wherein the controller is programed to perform the step of operating the video camera to obtain multiple successive AOIs and the step of analyzing each of the multiple successive AOIs are performed at a rate of over 1 kHz.

* * * * *